United States Patent [19]

Ige et al.

[11] Patent Number: 5,296,513
[45] Date of Patent: Mar. 22, 1994

[54] DENTAL COMPOSITION AND PROCESS FOR PRODUCING DENTAL POLYMERIC SHAPED ARTICLES

[75] Inventors: Hitoshi Ige; Nobuhiro Mukai; Naoto Ohsuga, all of Otake, Japan

[73] Assignee: Mitsubishi Rayon Co., Ltd., Tokyo, Japan

[21] Appl. No.: 915,880

[22] Filed: Jul. 20, 1992

Related U.S. Application Data

[63] Continuation of Ser. No. 555,479, Aug. 13, 1990, abandoned.

[30] Foreign Application Priority Data

Dec. 21, 1988 [JP] Japan .................. 63-322938

[51] Int. Cl.⁵ .................. A61K 6/08; C08F 20/10
[52] U.S. Cl. .................. 523/115; 523/116; 525/330.3; 525/355; 525/356
[58] Field of Search .................. 523/115, 116; 525/330.3, 355, 356; 526/318

[56] References Cited

U.S. PATENT DOCUMENTS

| | | | |
|---|---|---|---|
| 4,069,180 | 1/1978 | Chalmers | 525/356 |
| 4,342,677 | 8/1982 | Muramatsu et al. | 523/116 |
| 4,345,048 | 8/1982 | Friedli et al. | 525/326 |
| 4,755,620 | 7/1968 | Iwamoto et al. | 523/116 |
| 5,037,638 | 8/1991 | Hamer et al. | 523/116 |

FOREIGN PATENT DOCUMENTS

| | | |
|---|---|---|
| 1581263 | 9/1969 | France . |
| 2155375 | 5/1973 | France . |
| 504183 | 1/1975 | Japan . |
| 57-88106 | 6/1982 | Japan . |

*Primary Examiner*—Paul R. Michl
*Assistant Examiner*—LaVonda DeWitt
*Attorney, Agent, or Firm*—Cushman, Darby & Cushman

[57] ABSTRACT

Disclosed is a process for producing dental polymeric shaped articles resistant to the adhesion of plaque which comprises the steps of shaping and curing a dental composition containing a monomer having at least one (meth)acryloyloxy group, and bringing the cured product into contact with a halogen or a halogen compound. Also disclosed is a dental composition comprising a monomer having at least one (meth)acryloyloxy group and a polymerization initiator, which is characterized by having added thereto at least one of a halogen and a halogen compound. When cured, this dental composition produces dental polymeric shaped articles resistant to the adhesion of plaque.

10 Claims, No Drawings

DENTAL COMPOSITION AND PROCESS FOR PRODUCING DENTAL POLYMERIC SHAPED ARTICLES

This is a continuation of application Ser. No. 07/555,479, filed on Aug. 13, 1990, which was abandoned upon the filing hereof Ser. No. 07/915,880.

TECHNICAL FIELD

This invention relates to a process for producing dental polymeric shaped articles and to dental compositions. More particularly, it relates to a process for producing dental polymeric shaped articles which are resistant to the adhesion of plaque resulting from bacterial contamination because of the elimination of carbon-to-carbon double bonds remaining on the surface of the polymeric shaped articles, and to dental compositions in which few carbon-to-carbon double bonds remain when they are cured.

BACKGROUND ART

In the field of dental materials, the conversion from metallic materials to polymeric materials has been proceeding rapidly in recent years. Such dental materials include, for example, surface coating agents such as surface glazing agents and hard coating agents; composite resins such as filling composite resins, facing hard resins, composite inlays and jacket crowns; artificial teeth, denture bases and denture base liners; and orthodontic materials such as special impression tray materials and brackets.

These dental materials usually comprise a (meth)acrylate monomer and a polymerization initiator. Moreover, if need arises from the intended purpose, they can additionally contain inorganic materials, (meth)acrylate polymers, pigments, solvents, polymerization inhibitors, oxidation stabilizers and other additives. Typically, they are cured by photopolymerization by means of visible light or ultraviolet radiation, by thermal polymerization, or by redox polymerization. Moreover, the curing is often performed in the mouth.

In polymerizing these dental compositions, however, it is difficult to cause all double bonds to participate in the polymerization, so that some double bonds tend to remain. Moreover, when the polymerization is performed in the mouth, the presence of air cannot be avoided. Thus, the polymerization inhibiting effect of oxygen develops a tendency for a large amount of double bonds to remain, especially on the surface of the cured product. When a large number of double bonds remain on the surface of the cured product, the growth of bacteria on the surface of the cured product is promoted because of the presence of active sites comprising carbon-to-carbon double bonds. Thus, after the cured product has been used in the mouth for a long time, plaque resulting from bacterial contamination adheres to the cured product, causing a marked reduction in surface gloss and smoothness to impair its appearance and also posing a problem from the viewpoint of hygienics.

In order to minimize the polymerization inhibiting effect of oxygen, a number of methods using a water-soluble polymer (such as polyethylene glycol, polyvinyl pyrrolidone or polyvinyl alcohol) as an air barrier have been proposed, for example, in Japanese Patent Laid-Open Nos. 134705/'84 and 100505/'85. In these methods, an unpolymerized dental composition is applied, filled or formed into a desired shape, covered with the above-described polymer, and cured in the state shielded from oxygen. However, this is not very effective in preventing double bonds from remaining on the surface of the cured product, and cannot be regarded as a satisfactory measure to cope with the adhesion of plaque.

DISCLOSURE OF THE INVENTION

It is an object of the present invention to provide a process for producing dental polymeric shaped articles having excellent plaque resistance.

It is another object of the present invention to provide a dental composition which, even if used in ordinary formulations, can produce dental polymeric shaped articles having excellent plaque resistance.

According to one aspect of the present invention, there is provided a process for producing dental polymeric shaped articles which comprises the steps of shaping and curing a dental composition containing a monomer having at least one (meth)acryloyloxy group, and bringing the cured product into contact with a halogen or a halogen compound.

According to another aspect of the present invention, there is provided a dental composition comprising a monomer having at least one (meth)acryloyloxy group and a polymerization initiator, which is characterized by having added thereto at least one of a halogen or a halogen compound.

BEST MODE FOR CARRYING OUT THE INVENTION

The monomer having at least one (meth)acryloyloxy group, used in the process of the present invention, may be any monomer of the (meth)acrylate type. Although both monofunctional (meth)acrylates and polyfunctional (meth)acrylates [i.e., monomers having two or more (meth)acryloyloxy groups] can be used, it is preferable from the viewpoint of hardness characteristics desired for dental polymeric shaped articles that the dental composition contain a polyfunctional (meth)acrylate.

Examples of useful polyfunctional (meth)acrylates include ethylene glycol di(meth)acrylate, polyethylene glycol di(meth)acrylate having a degree of polymerization of 20 or less, 1,3-butanediol di(meth)acrylate, 1,4-butanediol di(meth)acrylate, 1,6-hexanediol di(meth)acrylate, glycerol di(meth)acrylate, bisphenol A diglycidyl di(meth)acrylate, ethoxylated bisphenol A di(meth)acrylates, urethane di(meth)acrylate, tetrafunctional urethane (meth)acrylates, trimethylolpropane tri(meth)acrylate, pentaerythritol tetra(meth)acrylate, dipentaerythritol penta(meth)acrylate, tri(meth)acrylates having an isocyanuric acid skeleton, and urethane hexa(meth)acrylates having an isocyanuric acid skeleton. Examples of useful monofunctional (meth)acrylates include methyl (meth)acryalte, ethyl (meth)acryalte, butyl (meth)acrylate, hydroxyethyl (meth)acrylate, benzyl (meth)acrylate, methoxyethyl (meth)acrylate, glycidyl (meth)acrylate, tetrahydrofurfuryl (meth)acrylate, and (meth)acryloyloxyethyltrimellitic acid or its anhydride.

Although these (meth)acrylate monomers may be used alone, they are preferably used in admixture of two or more.

The dental composition containing a monomer having at least one (meth)acryloyloxy group, used in the process of the present invention, may contain, in addition to the above-defined (meth)acrylate monomer(s), one or more vinyl monomers copolymerizable therewith. Specific examples of such monomers include styrene, acrylonitrile and vinyl acetate.

Where the dental composition contains both a polyfunctional monomer and a monofunctional monomer, the weight ratio of the polyfunctional monomer to the monofunctional monomer preferably ranges from 1:0.1 to 1:2.

The dental composition containing a monomer having at least one (meth)acryloyloxy group, used in the practice of the present invention, can additionally contain inorganic materials, (meth)acrylate polymers, pigments, solvents, polymerization inhibitors, oxidation stabilizers and other additives, according to the intended purpose. Examples of useful inorganic materials include quartz, silica and barium glass; examples of useful pigments include titanium oxide and iron oxide; and examples of useful solvents include alcohols (such as ethanol) and ethyl acetate.

In the process of the present invention, the above-described dental composition is either applied onto a denture or used for filling or coating purposes at a desired site in the mouth, and then cured. More specifically, where the dental composition is a surface coating agent such as a surface glazing agent or a hard coating agent, it is applied onto a tooth or a denture to form a coating film, which is then cured in that state. Where the dental composition is a composite resin, it is poured into the cavity of a tooth or used to replace the missing part thereof, or poured into a mold formed so as to conform to the cavity or missing part of a tooth, and then cured in that state. According to the manner of pouring, filling or application (hereinafter referred to collectively as shaping) and the purpose of use of the dental material, the type of monomer used may be suitably chosen in order to control the viscosity of the dental composition, and modify the surface hardness, smoothness and appearance of the cured product. Moreover, if necessary, one or more of the above-described additives may be used in combination therewith.

After being shaped, the above-described dental composition is cured. In this curing step, a polymerization initiator may be used as desired. The type of polymerization initiator used varies according to the polymerization technique employed. For thermal polymerization (i.e., polymerization by means of a radical initiator), various peroxides and azo compounds can be used. For photopolymerization by means of visible light or ultraviolet radiation), benzophenone and its derivatives, ketal compounds such as benzyl dimethyl ketal, benzoin alkyl ethers, anthraquinone and its derivatives, thioxanthone and its derivatives, acyl phosphine oxides and α-diketones can be used. Reducing agents such as amine compounds can also be used for purposes of photopolymerization. Moreover, redox polymerization can be performed by preparing the dental composition in two parts, one containing an oxidizing agent such as a peroxide and the other containing a reducing agent, and mixing them immediately before use.

In order to eliminate the carbon-to-carbon double bonds remaining on the surface of the resulting cured product (or polymeric shaped article), the process of the present invention brings the cured product into contact with at least one halogen or halogen compound that can add to the carbon-to-carbon double bonds. Examples of useful halogens include iodine and bromine, and examples of useful halogen compounds include highly active halogen compounds such as hydrogen halides, hypohalogenous acids and potassium iodide. Among them, halogens are preferred from the viewpoint of addition efficiency. Among the halogens, bromine and iodine are preferrdd from the viewpoint of handleability and toxicity, and iodine is especially preferred.

Although the halogen or halogen compound can be directly used for contact with the cured product, it may also be used in the form of a solution in a suitable solvent. The solvent should be substantially harmless to the human body because it is used in the mouth. For this reason, it is preferable to use an alcohol such as ethanol. When the halogen or halogen compound is used in the form of a solution, the concentration of the halogen or halogen compound may be chosen according to the treating method and treating conditions which will be described later. However, its concentration is usually not less than 0.01% by weight and preferably not less than 0.1% by weight. In order to control its viscosity from the viewpoint of handleability, the solution can contain a polymer soluble in the solvent used. For example, where ethanol is used as the solvent, usable polymers include polyethylene glycol, polyvinyl pyrrolidone, polyvinyl alcohol, polyvinyl acetate and the like.

Although the treatment by contact with a halogen or a halogen compound may be satisfactorily performed at room temperature, it is preferable to accelerate the reaction by heating and/or irradiation with light. Heating should be performed at temperatures which are not lower than 30° C and within a range causing no damage to the polymeric shaped article. Where the heating is performed in the mouth, the heating temperature should also be low enough to do no harm to the mouth. Heating at temperatures lower than 30° C will produce no distinct effect. In the case of heating in the mouth, the heating temperature is preferably not higher than 70° C. Where irradiation with light is performed, it is preferable to use light having wavelengths of 400 to 1,200 nm. Examples of lamps emitting light of such wavelengths include halogen lamps, xenon lamps, mercury vapor lamps and fluorescent lamps. Although the time of treatment by contact with a halogen or a halogen compound can vary according to the treating method, the treating temperature, and the use or nonuse of irradiation with light, it usually ranges from about 30 seconds to about 1 hour.

Instead of performing the treatment by contact with a halogen or a halogen compound to eliminate the double bonds remaining on the surface of the cured product, a similar result can be obtained by using a dental composition comprising a monomer having at least one (meth)acryloyloxy group and a polymerization initiator, to which at least one of a halogen and a halogen compound is added. More specifically, when this dental composition is shaped and cured, there is obtained a cured product in which no double bonds remain on the surface thereof.

The halogen or halogen compound used for this purpose can be any of the above-described halogens and halogen compounds. It is desirable that the halogen or halogen compound used not inhibit the polymerization of the dental composition to any appreciable extent. From this point of view, halogens are preferred and iodine is more preferred. The amount of halogen or halogen compound used should be suitably determined in consideration of the curability and color tone of the resulting dental composition. However, it should basically be within the range that imparts plaque resistance to the dental composition and does not impair the curability thereof. Typically, it is preferably within the range of 0.01 to 1.0 parts by weight, more preferably within the range of 0.05 to 0.5 parts, per 100 parts by weight of the (meth)acrylate monomer.

The present invention is further illustrated by the following examples. However, it is to be understood that the present invention is not limited thereto.

In these examples, all parts are by weight, unless otherwise specified. In each of the examples and comparative examples, three samples were prepared and evaluated.

Where the dental composition was a surface glazing and hardening agent, hardness was evaluated by applying the dental composition onto a polymethyl methacrylate plate so as to give a coating thickness of 10-50 μm, curing the coating, and measuring its pencil hardness. Where the dental composition was a composite resin, hardness was evaluated by curing the dental composition in the form of a disk having a diameter of 20 mm and a thickness of 1 mm, and measuring its Knoop hardness.

Whether the dental composition is a surface glazing and hardening agent or a composite resin, plaque resistance was evaluated by applying the dental composition onto a denture base so as to give a coating thickness of 10-50 μm, curing the coating, and putting the denture base to practical use in the mouth. After 1 week and after 3 months, the denture base was coated with a plaque stain (manufactured by GC Dental Industries Co., Ltd.) and the extent of plaque present thereon was examined visually. Thus, its plaque resistance was rated as good (○) when the denture base was not stained at all, or as poor (X) when the denture base was stained.

EXAMPLES 1-12 AND COMPARATIVE EXAMPLES 1-6

A surface glazing and hardening agent having the composition given below was prepared as a dental composition. This will hereinafter be referred to as dental composition I.

| | |
|---|---|
| Dipentaerythritol pentaacrylate | 2.2 parts |
| Tetrahydrofurfuryl acrylate | 0.6 part |
| Methyl methacrylate | 1.0 part |
| Benzyl dimethyl ketal | 0.1 part |

For each of the examples and comparative examples, three polymethyl methacrylate plates, measuring 20 mm (length)×20 mm (width)×2 mm (thickness), and three denture bases made of polymethyl methacrylate were provided as substrates. After the surfaces of these substrates were cleaned with ethanol, the aforesaid dental composition I was applied onto the substrates with a brush so as to give a coating thickness of 10-50 μm and then irradiated with light from a visible light irradiator α-Light; manufactured by Morita, Ltd.) for 10 minutes to obtain cured products. The surfaces of these cured products were treated with the treating agents listed in Table 1, and the surface hardness and plaque resistance thereof were evaluated. The results thus obtained are shown in Table 1.

TABLE 1

| | Surface treating solution | | | | Treating conditions | | | Results of evaluation | | |
|---|---|---|---|---|---|---|---|---|---|---|
| | | | | | | | | | Plaque resistance | |
| | Halogen compound | Solvent | Concentration (wt. %) | Viscosity modifier | Treating method | Temperature (°C.) | Light irradiator | Treating time (minutes) | Hardness | After 1 week | After 3 month |
| Example 1 | I$_2$ | Ethanol | 1.0 | — | D | 60 | — | 5 | 4H | ○ | ○ |
| Example 2 | Br$_2$ | Ethanol | 1.0 | — | D | 60 | — | 5 | 4H | ○ | ○ |
| Example 3 | KI | Ethanol | 1.0 | — | D | 60 | — | 20 | 4H | ○ | ○ |
| Example 4 | HI | Ethanol | 1.0 | — | D | 60 | G | 5 | 4H | ○ | ○ |
| Example 5 | I$_2$ | Ethyl acetate | 1.0 | — | D | 60 | — | 5 | 4H | ○ | ○ |
| Example 6 | I$_2$ | Ethanol | 0.01 | — | D | 60 | — | 20 | 4H | ○ | ○ |
| Example 7 | I$_2$ | Ethanol | 1.0 | PVP | C | 60 | — | 5 | 4H | ○ | ○ |
| Example 8 | I$_2$ | Ethanol | 1.0 | — | D | 30 | — | 20 | 4H | ○ | ○ |
| Example 9 | I$_2$ | Ethanol | 1.0 | PVP | C | — | E | 5 | 4H | ○ | ○ |
| Example 10 | I$_2$ | Ethanol | 1.0 | PVP | C | — | F | 2 | 4H | ○ | ○ |
| Example 11 | I$_2$ | Ethanol | 1.0 | PVP | C | — | G | 1 | 4H | ○ | ○ |
| Example 12 | I$_2$ | Ethanol | 1.0 | PVP | C | — | H | 1 | 4H | ○ | ○ |
| Comparative Example 1 | — | — | — | — | — | — | — | — | 4H | X | X |
| Comparative Example 2 | — | Ethanol | — | — | D | 60 | — | 30 | 4H | X | X |
| Comparative Example 3 | — | Ethanol | — | PVP | C | 60 | — | 30 | 4H | X | X |
| Comparative Example 4 | — | Ethanol | — | PVP | C | — | G | 30 | 5H | X | X |
| Comparative Example 5 | — | — | — | — | — | 60 | — | 30 | 4H | X | X |
| Comparative Example 6 | — | — | — | — | — | — | G | 30 | 5H | X | X |

(notes)
PVP: Polyvinyl pyrrolidone having a molecular weight of 50,000 used in an amount of 5 parts per 10 parts of solvent.
Treating method:
C = Coating;
D = Dipping.
Light irradiator:
E = Labolight LV-1 (manufactured by GC Dental Industries Co., Ltd.);
F = Permacure UC-1 (manufactured by GC Dental Industries Co., Ltd.);
G = α-Light (manufactured by Morita, Ltd.);
H = Dentacolor XS (manufactured by Kulzer AG).

EXAMPLES 13-24 AND COMPARATIVE EXAMPLES 7-12

Cured products were obtained in the same manner as in Example 1, except that a surface glazing and hardening agent having the composition given below (hereinafter referred to as dental composition II) was used in place of dental composition I. These cured products were treated with the treating agents listed in Table 2 and then evluated in the same manner as in Example 1.

| | |
|---|---|
| Isocyanuric acid-based triacrylate having the structural formula given below | 3.0 parts |
| Methyl methacrylate | 2.0 parts |
| Benzoin methyl ether | 0.1 part |

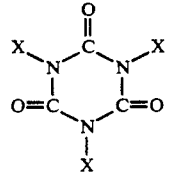

X: $-(CH_2)_2-OCOCH=CH_2$

The results thus obtained are shown in Table 2.

EXAMPLES 25-36 AND COMPARATIVE EXAMPLES 13-18

Cured products were obtained in the same manner as in Example 1, except that a dental composition comprising solutions A and B having the compositions given below (hereinafter referred to as dental composition III) was used in place of dental composition I, and that it was subjected to redox polymerization by mixing the two solutions and allowing the mixture to stand at room temperature, instead of being photopolymerized. These cured products were treated with the treating agents listed in Table 3 and then evaluated in the same manner as in Example 1. The results thus obtained are shown in Table 3.

| | |
|---|---|
| (Solution A) | |
| Dipentaerythritol pentaacrylate | 2.4 parts |
| Tetrahydrofurfuryl acrylate | 0.6 part |
| Methyl methacrylate | 1.0 part |
| Benzoyl peroxide | 0.1 part |
| (Solution B) | |
| Dipentaerythritol pentaacrylate | 2.4 parts |
| Tetrahydrofurfuryl acrylate | 0.6 part |
| Methyl methacrylate | 1.0 part |
| p-Tolyldiethanolamine | 0.2 part |

TABLE 2

| | Surface treating solution | | | | Treating conditions | | | | Results of evaluation | | |
|---|---|---|---|---|---|---|---|---|---|---|---|
| | Halogen compound | Solvent | Concentration (wt. %) | Viscosity modifier | Treating method | Temperature (°C.) | Light irradiator | Treating time (minutes) | Hardness | Plaque resistance After 1 week | After 3 month |
| Example 13 | I$_2$ | Ethanol | 1.0 | — | D | 60 | — | 5 | 3H | ○ | ○ |
| Example 14 | Br$_2$ | Ethanol | 1.0 | — | D | 60 | — | 5 | 3H | ○ | ○ |
| Example 15 | KI | Ethanol | 1.0 | — | D | 60 | — | 20 | 3H | ○ | ○ |
| Example 16 | HI | Ethanol | 1.0 | — | D | — | G | 5 | 3H | ○ | ○ |
| Example 17 | I$_2$ | Ethyl acetate | 1.0 | — | D | 60 | — | 5 | 3H | ○ | ○ |
| Example 18 | I$_2$ | Ethanol | 0.01 | — | D | 60 | — | 20 | 3H | ○ | ○ |
| Example 19 | I$_2$ | Ethanol | 1.0 | PVP | C | 60 | — | 5 | 3H | ○ | ○ |
| Example 20 | I$_2$ | Ethanol | 1.0 | — | D | 30 | — | 20 | 3H | ○ | ○ |
| Example 21 | I$_2$ | Ethanol | 1.0 | PVP | C | — | E | 5 | 3H | ○ | ○ |
| Example 22 | I$_2$ | Ethanol | 1.0 | PVP | C | — | F | 2 | 3H | ○ | ○ |
| Example 23 | I$_2$ | Ethanol | 1.0 | PVP | C | — | G | 1 | 3H | ○ | ○ |
| Example 24 | I$_2$ | Ethanol | 1.0 | PVP | C | — | H | 1 | 3H | ○ | ○ |
| Comparative Example 7 | — | — | — | — | — | — | — | — | 3H | X | X |
| Comparative Example 8 | — | Ethanol | — | — | D | 60 | — | 30 | 3H | X | X |
| Comparative Example 9 | — | Ethanol | — | PVP | C | 60 | — | 30 | 3H | X | X |
| Comparative Example 10 | — | Ethanol | — | PVP | C | — | G | 30 | 4H | X | X |
| Comparative Example 11 | — | — | — | — | — | 60 | — | 30 | 3H | X | X |
| Comparative Example 12 | — | — | — | — | — | — | G | 30 | 4H | X | X |

TABLE 3

| | Surface treating solution | | | | Treating conditions | | | | Results of evaluation | | |
|---|---|---|---|---|---|---|---|---|---|---|---|
| | Halogen compound | Solvent | Concentration (wt. %) | Viscosity modifier | Treating method | Temperature (°C.) | Light irradiator | Treating time (minutes) | Hardness | Plaque resistance After 1 week | After 3 month |
| Example 25 | I$_2$ | Ethanol | 1.0 | — | D | 60 | — | 5 | 4H | ○ | ○ |
| Example 26 | Br$_2$ | Ethanol | 1.0 | — | D | 60 | — | 5 | 4H | ○ | ○ |
| Example 27 | KI | Ethanol | 1.0 | — | D | 60 | — | 20 | 4H | ○ | ○ |
| Example 28 | HI | Ethanol | 1.0 | — | D | — | G | 20 | 4H | ○ | ○ |
| Example 29 | I$_2$ | Ethyl acetate | 1.0 | — | D | 60 | — | 5 | 4H | ○ | ○ |
| Example 30 | I$_2$ | Ethanol | 0.01 | — | D | 60 | — | 20 | 4H | ○ | ○ |
| Example 31 | I$_2$ | Ethanol | 1.0 | PVP | C | 60 | — | 5 | 4H | ○ | ○ |
| Example 32 | I$_2$ | Ethanol | 1.0 | — | D | 30 | — | 20 | 4H | ○ | ○ |
| Example 33 | I$_2$ | Ethanol | 1.0 | PVP | C | — | E | 5 | 4H | ○ | ○ |

TABLE 3-continued

| | Surface treating solution | | | | Treating conditions | | | | Results of evaluation | | |
|---|---|---|---|---|---|---|---|---|---|---|---|
| | Halogen compound | Solvent | Concentration (wt. %) | Viscosity modifier | Treating method | Temperature (°C.) | Light irradiator | Treating time (minutes) | Hardness | Plaque resistance | |
| | | | | | | | | | | After 1 week | After 3 month |
| Example 34 | I₂ | Ethanol | 1.0 | PVP | C | — | F | 2 | 4H | ◯ | ◯ |
| Example 35 | I₂ | Ethanol | 1.0 | PVP | C | — | G | 1 | 4H | ◯ | ◯ |
| Example 36 | I₂ | Ethanol | 1.0 | PVP | C | — | H | 1 | 4H | ◯ | ◯ |
| Comparative Example 13 | — | — | — | — | — | — | — | — | 4H | X | X |
| Comparative Example 14 | — | Ethanol | — | — | D | 60 | — | 30 | 4H | X | X |
| Comparative Example 15 | — | Ethanol | — | PVP | C | 60 | — | 30 | 4H | X | X |
| Comparative Example 16 | — | Ethanol | — | PVP | C | — | G | 30 | 5H | X | X |
| Comparative Example 17 | — | — | — | — | — | 60 | — | 30 | 4H | X | X |
| Comparative Example 18 | — | — | — | — | — | — | G | 30 | 5H | X | X |

EXAMPLES 37 AND 38 AND COMPARATIVE EXAMPLES 19 AND 20

A filling composite resin having the composition given below (hereinafter referred to as dental composition IV) was used as a dental composition. Using 1 mm thick stainless steel plates having a hole of 20 mm diameter, composite resin disks having a diameter of 20 mm and a thickness of 1 mm were formed by pouring the composite resin into the hole and irradiating it with light from a visible light irradiator (α-Light) for 10 minutes. Separately, the composite resin was applied onto polymethyl methacrylate denture bases and cured in the same manner as in Example 1. The resulting cured products were treated with the treating agents listed in Table 4. Then, the Knoop hardness of the disks and the plaque resistance of the denture bases were evaluated. The results thus obtained are shown in Table 4.

| 2,2-Bis[4-(3-methacryloyloxy-2-hydroxypropoxy)phenyl]propane | 0.8 part |
|---|---|
| Triethylene glycolmethacrylate (hereinafter referred to as 3G) | 1.2 parts |
| Silane-treated quartz powder (quartz powder with an average particle diameter of 12 μm or less having 2% by weight of γ-methacryloyloxypropyl trimethoxy silane added thereto) | 8.0 parts |
| Camphorquinone | 0.01 part |
| Dimethylaminoethyl methacrylate | 0.04 part |

EXAMPLES 39 AND 40 AND COMPARATIVE EXAMPLES 21 AND 22

The procedure of Example 37 was repeated, except that a filling composite resin having the composition given below was used in place of dental composition IV and the resulting cured products were treated as shown in Table 4. The results thus obtained are shown in Table 4.

| Ethoxylated bisphenol A dimethacrylate | 1.2 parts |
|---|---|
| Isocyanuric acid-based urethane hexaacrylate having the structural formula given below | 0.4 part |
| 3G | 0.4 part |
| Silane-treated quartz powder (same as used in Example 37) | 8.0 parts |
| Camphorquinone | 0.01 part |
| Isoamyl p-dimethylaminobenzoate | 0.04 part |

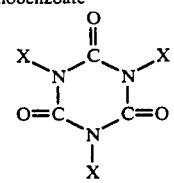

X: —(CH₂)₆—NHCOOCH(CH₂OCOCH=CH₂)₂

EXAMPLES 41 AND 42 AND COMPARATIVE EXAMPLES 23 AND 24

Cured products were prepared in the same manner as in Example 37, except that a facing hard resin having the composition given below (hereinafter referred to as dental composition V) was used as a dental composition and it was thermally polymerized at 60° C. for 5 hours. These cured products were treated as shown in Table 4, and then evaluated. The results thus obtained are shown in Table 4.

| Urethane diacrylate having the structural formula given below | 1.2 parts |
|---|---|
| 3G | 0.8 part |
| Finely powdered silica (with an average particle diameter of 0.04 μm) | 2.0 parts |
| Benzoyl peroxide | 0.04 part |

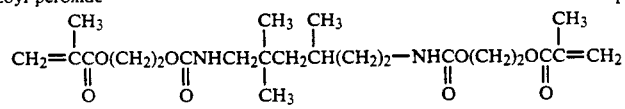

TABLE 4

| | Surface treating solution | | | | Treating conditions | | | | Results of evaluation | | |
|---|---|---|---|---|---|---|---|---|---|---|---|
| | Halogen compound | Solvent | Concentration (wt. %) | Viscosity modifier | Treating method | Temperature (°C.) | Light irradiator | Treating time (minutes) | Hardness (HK) | Plaque resistance | |
| | | | | | | | | | | After 1 week | After 3 month |
| Example 37 | I₂ | Ethanol | 1.0 | — | D | 60 | — | 5 | 85 | ○ | ○ |
| Example 38 | I₂ | Ethanol | 1.0 | PVP | C | — | G | 1 | 86 | ○ | ○ |
| Example 39 | I₂ | Ethanol | 1.0 | — | D | 60 | — | 5 | 92 | ○ | ○ |
| Example 40 | I₂ | Ethanol | 1.0 | PVP | C | — | G | 1 | 90 | ○ | ○ |
| Example 41 | I₂ | Ethanol | 1.0 | — | D | 60 | — | 5 | 66 | ○ | ○ |
| Example 42 | I₂ | Ethanol | 1.0 | PVP | C | — | G | 1 | 63 | ○ | ○ |
| Comparative Example 19 | — | — | — | — | — | — | — | — | 84 | X | X |
| Comparative Example 20 | — | Ethanol | — | — | D | 60 | — | 30 | 83 | X | X |
| Comparative Example 21 | — | — | — | — | — | — | — | — | 91 | X | X |
| Comparative Example 22 | — | Ethanol | — | — | D | 60 | — | 30 | 92 | X | X |
| Comparative Example 23 | — | — | — | — | — | — | — | — | 65 | X | X |
| Comparative Example 24 | — | Ethanol | — | — | D | 60 | — | 30 | 64 | X | X |

EXAMPLES 43–48

Surface glazing and hardening agents were prepared by adding each of the halogens or halogen compounds listed in Table 5 to dental composition I in the amount shown in Table 5.

For each example, three polymethyl methacrylate plates, measuring 20 mm (length)×20 mm (width)×2 mm (thickness), and three denture bases made of polymethyl methacrylate were provided as substrates. After the surfaces of these substrates were cleaned with ethanol, each of the aforesaid surface glazing and hardening agents was applied onto the substrates with a brush so as to give a coating thickness of 10–50 μm and then irradiated with light from a visible light irradiator (α-Light) for 10 minutes to obtain cured products. The surface hardness and plaque resistance of these cured products were evaluate and the results thus obtained are shown in Table 5.

TABLE 5

| | Halogen compound | Amount added* (wt. %) | Hardness | Plaque resistance | |
|---|---|---|---|---|---|
| | | | | After 1 week | After 3 months |
| Example 43 | I₂ | 0.2 | 4H | ○ | ○ |
| Example 44 | Br₂ | 0.2 | 4H | ○ | ○ |
| Example 45 | KI | 0.2 | 4H | ○ | ○ |
| Example 46 | HI | 0.2 | 4H | ○ | ○ |
| Example 47 | I₂ | 0.05 | 4H | ○ | ○ |
| Example 48 | I₂ | 0.5 | 4H | ○ | ○ |

*Weight percentage based on the amount of the (meth)acrylate monomer.

EXAMPLES 49–54

Surface glazing and hardening agents were prepared by adding each of the halogen or halogen compounds listed in Table 6 to dental composition II in the amount shown in Table 6. Then, cured products were obtained in the same manner as in Example 43, except that the aforesaid surface glazing and hardening agents were used. These cured products were evaluated in the same manner as in Example 43 and the results thus obtained are shown in Table 6.

TABLE 6

| | Halogen compound | Amount added* (wt. %) | Hardness | Plaque resistance | |
|---|---|---|---|---|---|
| | | | | After 1 week | After 3 months |
| Example 49 | I₂ | 0.2 | 3H | ○ | ○ |
| Example 50 | Br₂ | 0.2 | 3H | ○ | ○ |
| Example 51 | KI | 0.2 | 3H | ○ | ○ |
| Example 52 | HI | 0.2 | 3H | ○ | ○ |
| Example 53 | I₂ | 0.05 | 3H | ○ | ○ |
| Example 54 | I₂ | 0.5 | 3H | ○ | ○ |

*Weight percentage based on the amount of the (meth)acrylate monomer.

EXAMPLES 55–60

Each of the halogens or halogen compounds listed in Table 7 was added to solutions A and B of dental composition III in the amount shown in Table 6. Then, cured products were obtained in the same manner as in Example 43, except that the aforesaid solutions were mixed and the resulting mixture was subjected to redox polymerization by allowing it to stand at room temperature. These cured products were evaluated in the same manner as in Example 43 and the results thus obtained are shown in Table 7.

TABLE 7

| | Halogen compound | Amount added* (wt. %) | Hardness | Plaque resistance | |
|---|---|---|---|---|---|
| | | | | After 1 week | After 3 months |
| Example 55 | I₂ | 0.2 | 4H | ○ | ○ |
| Example 56 | Br₂ | 0.2 | 4H | ○ | ○ |
| Example 57 | KI | 0.2 | 4H | ○ | ○ |
| Example 58 | HI | 0.2 | 4H | ○ | ○ |
| Example 59 | I₂ | 0.05 | 4H | ○ | ○ |
| Example 60 | I₂ | 0.5 | 4H | ○ | ○ |

*Weight percentage based on the amount of the (meth)acrylate monomer.

EXAMPLES 61–66

Filling composite resins were prepared by adding each of the halogens or halogen compounds listed in Table 8 to dental composition IV in the amount shown in Table 8. Using 1 mm thick stainless steel plates having a hole of 20 mm diameter, composite resin disks having a diameter of 20 mm and a thickness of 1 mm were formed by pouring each of the aforesaid composite resins into the hole and irradiating it with light from a visible light irradiator (α-Light) for 10 minutes. Separately, the aforesaid composite resins were applied onto polymethyl methacrylate denture bases and cured in the same manner as in Example 43. Then, the Knoop hardness of the disks and the plaque resistance of the denture bases were evaluated. The results thus obtained are shown in Table 8.

TABLE 8

| | Halogen compound | Amount added* (wt. %) | Hardness | Plaque resistance After 1 week | Plaque resistance After 3 months |
| --- | --- | --- | --- | --- | --- |
| Example 61 | $I_2$ | 0.2 | 86 | ◯ | ◯ |
| Example 62 | $Br_2$ | 0.2 | 84 | ◯ | ◯ |
| Example 63 | KI | 0.2 | 85 | ◯ | ◯ |
| Example 64 | HI | 0.2 | 83 | ◯ | ◯ |
| Example 65 | $I_2$ | 0.05 | 84 | ◯ | ◯ |
| Example 66 | $I_2$ | 0.5 | 85 | ◯ | ◯ |

*Weight percentage based on the amount of the (meth)acrylate monomer.

EXAMPLES 67-72

Facing hard resins were prepared by adding each of the halogens or halogen compounds listed in Table 9 to dental composition V in the amount shown in Table 9. Then, cured products were obtained in the same manner as in Example 61, except that the aforesaid facing hard resins were polymerized at 60° C for 5 hours. These cured products were evaluated in the same manner as in Example 61 and the results thus obtained are shown in Table 9.

TABLE 9

| | Halogen compound | Amount added* (wt. %) | Hardness | Plaque resistance After 1 week | Plaque resistance After 3 months |
| --- | --- | --- | --- | --- | --- |
| Example 67 | $I_2$ | 0.2 | 66 | ◯ | ◯ |
| Example 68 | $Br_2$ | 0.2 | 63 | ◯ | ◯ |
| Example 69 | KI | 0.2 | 64 | ◯ | ◯ |
| Example 70 | HI | 0.2 | 64 | ◯ | ◯ |
| Example 71 | $I_2$ | 0.05 | 65 | ◯ | ◯ |
| Example 72 | $I_2$ | 0.5 | 63 | ◯ | ◯ |

*Weight percentage based on the amount of the (meth)acrylate monomer.

We claim:

1. A process for producing dental polymeric shaped articles which comprises the steps of shaping and curing a dental composition containing a monomer having at least one (meth)acryloyloxy group, a polyfunctional monomer having two or more (meth)acryloyloxy groups and a monofunctional monomer wherein the weight ratio of the polyfunctional monomer to the monofunctional monomer ranges from 1:0.1 to 1:2, and bringing the cured product into contact with a halogen or a halogen compound selected from the group consisting of $I_2$, $Br_2$, $Br_2$, KI and HI.

2. A process for producing dental polymeric shaped articles as claimed in claim 1 wherein the dental composition contains a monomer having two or more (meth)acryloyloxy groups.

3. A process for producing dental polymeric shaped articles as claimed in claim 1 or 2 wherein the halogen is bromine or iodine.

4. A dental composition comprising a monomer having at least one (meth)acryloyloxy group, a polyfunctional monomer having two or more (meth)acryloyloxy groups and a monofunctional monomer wherein the weight ratio of the polyfunctional monomer to the monofunctional monomer ranges from 1:0.1 to 1:2, and a polymerization initiator, which is characterized by having added thereto at least one of a halogen and a halogen compound selected from the group consisting of $I_2$, $Br_2$, KI and HI.

5. A dental composition as claimed in claim 4 which contains a monomer having two or more (meth)acryloyloxy groups.

6. A process for producing dental polymeric shaped articles as claimed in claim 1 wherein the halogen or halogen compound selected from a group consisting of $I_2$, $Br_2$, KI and HI is used in the form of a solution in a solvent.

7. A process for producing dental polymeric shaped articles as claimed in claim 6 wherein the solvent is an alcohol.

8. A process for producing dental polymeric shaped articles as claimed in claim 6 wherein the concentration of the solution is not less than 0.1% by weight.

9. A process for producing dental polymeric shaped articles as claimed in claim 6 wherein the solution contains a polymer soluble in the solvent used.

10. A dental composition as claimed in claim 4 wherein the halogen or halogen compound selected from a group consisting of $I_2$, $Br_2$, KI and HI is within the range of 0.01 to 1.0 parts by weight per 100 parts by weight of the monomer having at least one (meth)acryloyloxy group.

* * * * *